(12) United States Patent
Kucklick (10) Patent No.: US 8,357,126 B2
(45) Date of Patent: Jan. 22, 2013

(54) ANTI-EXTRAVASATION CATHETER

(75) Inventor: Theodore R. Kucklick, Los Gatos, CA (US)

(73) Assignee: Cannuflow, Inc., San Jose, CA (US)

( * ) Notice: Subject to any disclaimer, the term of this patent is extended or adjusted under 35 U.S.C. 154(b) by 1083 days.

(21) Appl. No.: 11/585,716

(22) Filed: Oct. 24, 2006

(65) Prior Publication Data
US 2008/0172013 A1    Jul. 17, 2008

(51) Int. Cl.
*A61M 5/00* (2006.01)

(52) U.S. Cl. .................................................. 604/264

(58) Field of Classification Search ............. 604/288.01, 604/264, 288.03, 175, 114, 156, 105, 28
See application file for complete search history.

(56) References Cited

U.S. PATENT DOCUMENTS

| | | | | |
|---|---|---|---|---|
| 4,044,793 | A | * | 8/1977 | Krueger et al. ............... 137/881 |
| 4,333,452 | A | * | 6/1982 | Au ........................... 128/205.24 |
| 4,646,722 | A | | 3/1987 | Silverstein et al. |
| 4,717,379 | A | * | 1/1988 | Ekholmer ..................... 604/43 |
| 4,973,321 | A | * | 11/1990 | Michelson .................... 604/523 |
| 5,394,886 | A | * | 3/1995 | Nabai et al. .................... 600/567 |
| 5,586,629 | A | * | 12/1996 | Shoberg et al. ................. 141/21 |
| 5,848,882 | A | * | 12/1998 | Hashimoto et al. ........... 417/569 |
| 6,039,078 | A | * | 3/2000 | Tamari ........................... 138/30 |
| 6,980,852 | B2 | * | 12/2005 | Jersey-Willuhn et al. .... 600/547 |
| 2003/0093029 | A1 | | 5/2003 | McGuckin, Jr. et al. |
| 2003/0204161 | A1 | * | 10/2003 | Ferek-Petric ................... 604/20 |
| 2005/0004584 | A1 | | 1/2005 | Franco et al. |

FOREIGN PATENT DOCUMENTS

| | | |
|---|---|---|
| JP | 2005502387 A | 1/2005 |
| JP | 2005532841 A | 11/2005 |
| WO | 2006105283 A2 | 10/2006 |

OTHER PUBLICATIONS

Subclavian vein. Oct. 20, 2005. Wikipedia.com. Jun. 30, 2009 <http://en.wikipedia.org/wiki/Subclavian_vein>.*
Casey, Kevin, et al. "Brachial versus basilic vein dialysis fistulas: a comparison of maturation and patency rates." Journal of Vascular Surgery. 47.2 (2008): 402-406. Feb. 2008 <http://www.ncbi.nlm.nih.gov/pubmed/18241763>.*

* cited by examiner

*Primary Examiner* — Nicholas Lucchesi
*Assistant Examiner* — Weng Lee
(74) *Attorney, Agent, or Firm* — Susan L. Crockett, Esq.; K. David Crockett, Esq.; Crockett & Crockett, PC (57) ABSTRACT

The disclosed devices and methods provide for the minimization of fluid extravasation during use of infusion catheters such as peripherally inserted central catheters and central venous catheters. The anti-extravasation catheter allows a surgeon to drain fluids from soft tissue surrounding an infusion site while also providing fluid inflow to a patient.

12 Claims, 7 Drawing Sheets

ANTI-EXTRAVASATION CATHETER

FIELD OF THE INVENTIONS

The inventions described below relate the field of catheters and more specifically, to catheters inserted into the central venous system.

BACKGROUND OF THE INVENTIONS

An infusion catheter, such as a peripheral intravenous catheter, is a thin flexible tube that is inserted into a peripheral vein, usually in the bend of the arm of a patient. Once inserted, the infusion catheter is threaded along the peripheral vein with the tip ideally positioned for infusion of fluids where they can be quickly diluted. Peripheral catheters as well as other types of catheters including peripherally inserted central catheters, central venous catheters and Hickman lines can remain in place for extended periods of time within a patient (up to six months). Infusion catheters have been available for many years and are typically used to administer fluids such as parenteral nutrition, chemotherapy, vasopressor (adrenalin-like medications), antibiotics and other hypertonic/caustic solutions. These catheters may also be used for blood draws. The use of such catheters avoids the complications associated with the direct puncture of the central venous circulation system. However, using a peripherally inserted central catheter to administer fluids to a patient is not without its drawbacks.

A common problem with the infusion of solutions into a patient is extravasation. Extravasation is the collection of interstitial fluid such as blood, nutritional fluids or medications into tissue surrounding an infusion site. Fluid escaping into the soft tissues surrounding the infusion site can have adverse effects on the patient. Some of these effects include the forming of blood clots in veins (thrombophlebitis), arterial injury, nerve injury, the compression of blood vessels and nerves and infection.

Extravasation of certain medications can also lead to other injuries commonly referred to as "IV burns." Leakage of cytotoxic drugs, intravenous nutrition, solutions of calcium, potassium, bicarbonate and even dextrose solutions outside the vein can cause skin necrosis. Other complications may include scarring around tendons, nerves and joints, especially on the dorsum of the hand or in the antecubital region. Extravasation may even cause skin loss above the area of injury and may require skin grafting.

In cancer treatment, accidental extravasation is a feared complication, especially from drugs such as the anthracyclines, mitomycin, vincristine, and vinoorelbine, which are examples of vessicant drugs. Vessicant drugs cause tissue destruction upon infiltration. In this context, extravasation is the unintended presence of a vessicant outside the vascular bed or vasculature.

Accidental extravasation has been estimated to occur in up to 6% of all patients receiving chemotherapy. Chemotherapeutic agents, such as the anthracyclines, are especially likely to cause severe tissue damage on extravasation. The tissue injury may not appear for several days or even weeks, but when it appears it may continue to worsen for months, due to drug recycling into adjacent tissue.

The danger of the adverse effects as well as kinks or clogs in the catheter may require catheters to be removed from a patient and reinserted in another location. Furthermore, extravasation may result in longer recovery time, pain and discomfort in patients. Because of the effects caused by extravasation, devices and methods are needed to reduce extravasation caused by the use of infusion.

SUMMARY

The devices and methods shown below provide for the minimization of fluid extravasation during use of infusion catheters including peripheral catheters and central venous catheters. The anti-extravasation catheter allows a surgeon to drain fluids from soft tissue surrounding an insertion point or an infusion site while also providing fluid inflow to a patient.

The anti-extravasation catheter comprises a multi-lumen flexible tube characterized by a distal end, a distal end, a proximal portion and a distal portion. The proximal end of the tube is provided with fluid ports, a manifold and other means of controlling the flow of fluid inside the tube. The distal portion of the tube is provided with one or more outflow holes. The proximal portion of the tube is provided with a plurality of drainage apertures. Each drainage aperture communicates with one or more drainage lumens inside the tube, thereby allowing fluid to drain from the tissue surrounding the insertion point of the catheter to sinks or vacuum sources located outside the patient. When the anti-extravasation catheter is disposed within the patient, the drainage holes are placed in fluid communication with tissue in contact with the infusion site. The anti-extravasation catheter allows a physician to administer solutions to the patient while reducing the amount of fluid extravasation occurring in tissue surrounding the insertion point near the site of infusion.

DETAILED DESCRIPTION OF THE INVENTION

Figure 1:
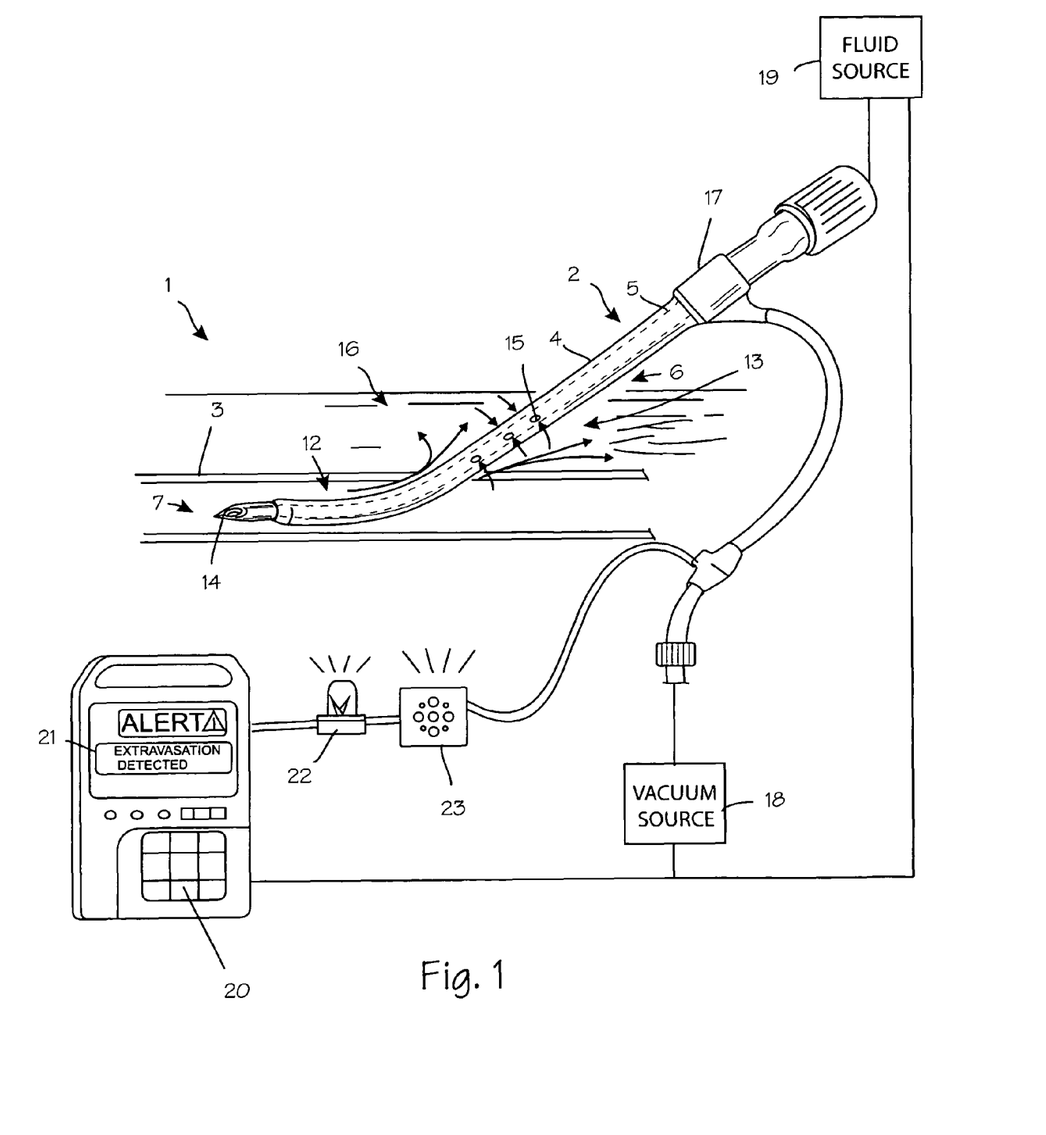
FIG. 1 is a patient with an anti-extravasation catheter inserted into a peripheral vein.

FIG. 1 is a patient 1 with an anti-extravasation catheter 2 inserted into a peripheral vein 3. The anti-extravasation catheter comprises a tube 4 having a central lumen 5 (shown in phantom) extending from the proximal end to the distal end. The tube has a length and an outer diameter suitable for extending from an insertion point 6 on a patient to a treatment/infusion site 7. The insertion point is the place where the catheter is inserted in a patient. The infusion site is the area in the body where the catheter infuses a fluid. A peripheral intravenous catheter typically comprises a shorter tube (a few centimeters long) inserted through the skin into a peripheral vein. In the case of a peripherally inserted central catheter, the tube will be sized and dimensioned to extend from a peripheral insertion point to the central venous system including the superior vena cava or the right atrium. When the infusion catheter is a central venous catheter, the tube is sized and dimensioned to extend from a subclavian, internal jugular or a femoral vein to the superior vena cava or right atrium. The tube is constructed of a material suitable for insertion into the venous system of a patient such as silicone, nylon, polycarbonate urethane, polyurethane, polydimethylsiloxane and polyethylene glycol.

The length of the tube 4 is characterized by a distal section 12 (the venous section) and a proximal interstitial section 13 (the interstitial section). The distal end of the tube may contain a hollow penetrating element 14 in fluid communication with the central lumen 5 to facilitate insertion of the catheter into the patient. The proximal (interstitial) section of the tube is provided with a plurality of drainage apertures 15. The proximal section of the tube is placed in contact with tissue 16 surrounding the insertion point and the peripheral vein 3 of the patient when the catheter 2 is disposed within the patent 1. The drainage apertures 15 are disposed in such a way that the apertures 15 are placed in fluid communication with tissue surrounding the insertion point where interstitial fluid collection may occur when the catheter is in use. Each drainage aperture 15 communicates with one or more drainage lumens disposed within the tube, thereby allowing fluid to drain from the tissue surrounding the insertion point to a vacuum source or sinks located outside the patient in fluid communication with the drainage lumens.

The proximal end of the tube is provided with a manifold or hub 17. The hub is in fluid communication with the central lumen and the drainage lumens. The hub is adapted for coupling to a vacuum source 18 and fluid source 19. The fluid source is placed in fluid communication with the central lumen of the catheter through the hub to facilitate the flow of fluids into the patient. The vacuum source is placed in fluid communication with the drainage lumens to facilitate removal of interstitial fluid. A control system 20 may be operably connected to the fluid source to deliver fluid and to the vacuum source to remove interstitial fluid by activating the vacuum source. Interstitial fluid is removed through one or more drainage apertures in fluid communication with the drainage lumens and the vacuum source. The control system may also be provided with a display 21 was well as an audio 22 and/or visual 23 warning system that indicates when extravasation is occurring.

Figure 2:
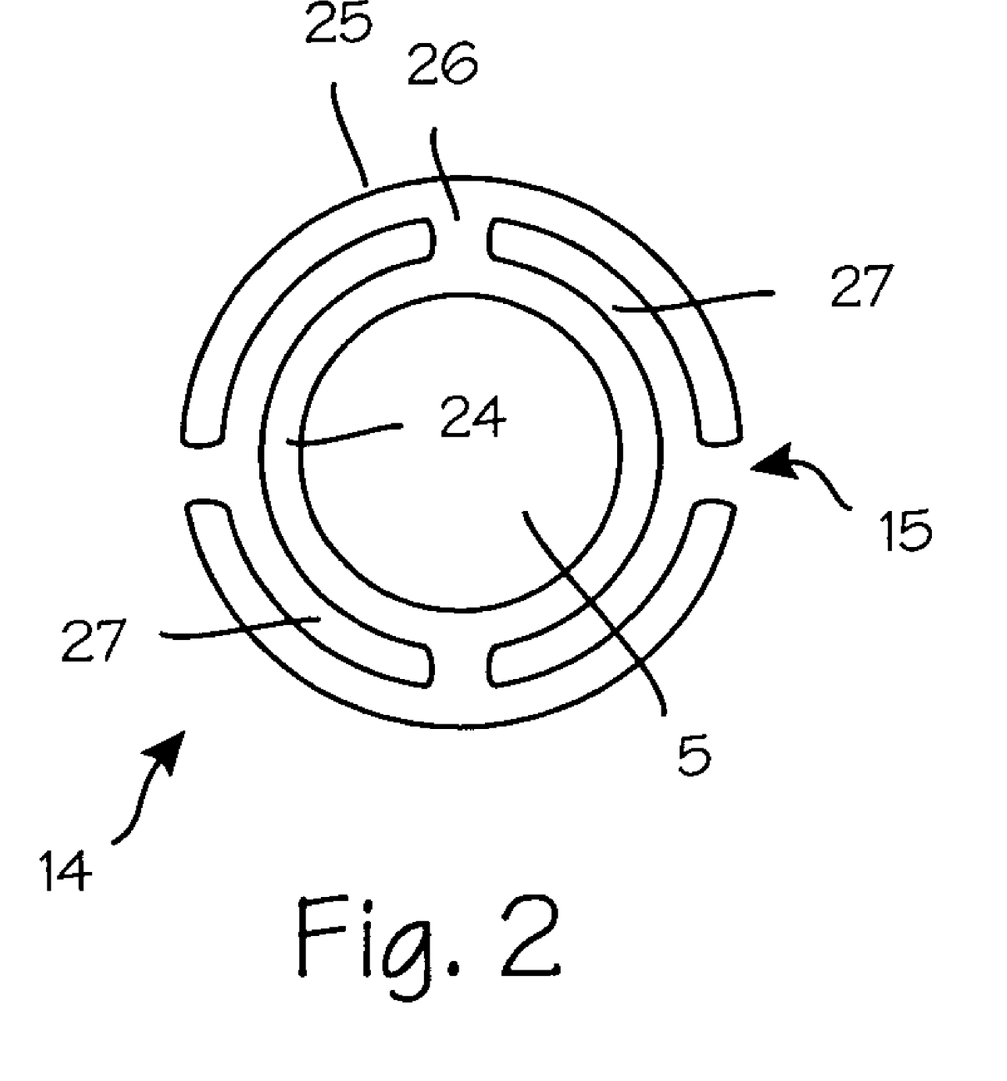
FIG. 2 is a cross-sectional view of the anti-extravasation catheter.

FIG. 2 is a cross-sectional view of the anti-extravasation catheter. As seen in FIG. 2, the tube 4 comprises an inner tube 24 and an outer tube 25 disposed about the outer tube and one or more ribs 26 extending between the inner tube and outer tube. The inner tube, the outer tube and the plurality of ribs bound one or more drainage lumens 27 disposed between the inner tube and the outer tube that extend longitudinally along the tube 4. Drainage apertures 15 are in fluid communication with one or more drainage lumens disposed within the tube.

Figure 3:
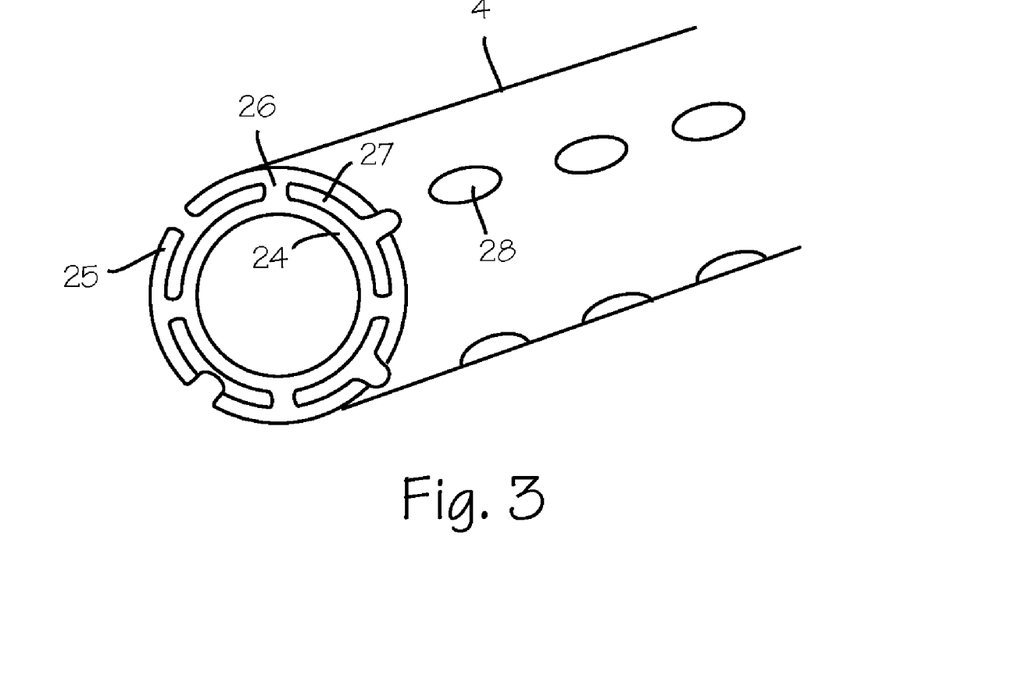
FIG. 3 is a sectional view of the proximal portion of the catheter wherein the drainage apertures are comprised of a pattern of substantially circular fenestrations.

Drainage apertures 15 may comprise a variety of patterns or configurations that allow for the effective removal of interstitial fluid. The size and pattern of the drainage apertures can be used to regulate fluid removal. FIG. 3 is a view of the proximal portion of the tube 4 wherein the drainage apertures are comprised of a pattern substantially circular fenestrations 28. The tube 4 has one or more drainage lumens disposed within the tube and running longitudinally along the catheter tube. A plurality of ribs 26 project from the inner tube 24 to the outer tube 25 forming the plurality of drainage lumens 27. Substantially circular fenestrations are disposed along the proximal portion of the outer tube. Each substantially circular fenestration communicates with one or more drainage lumens 27 disposed within the tube.

Figure 4:
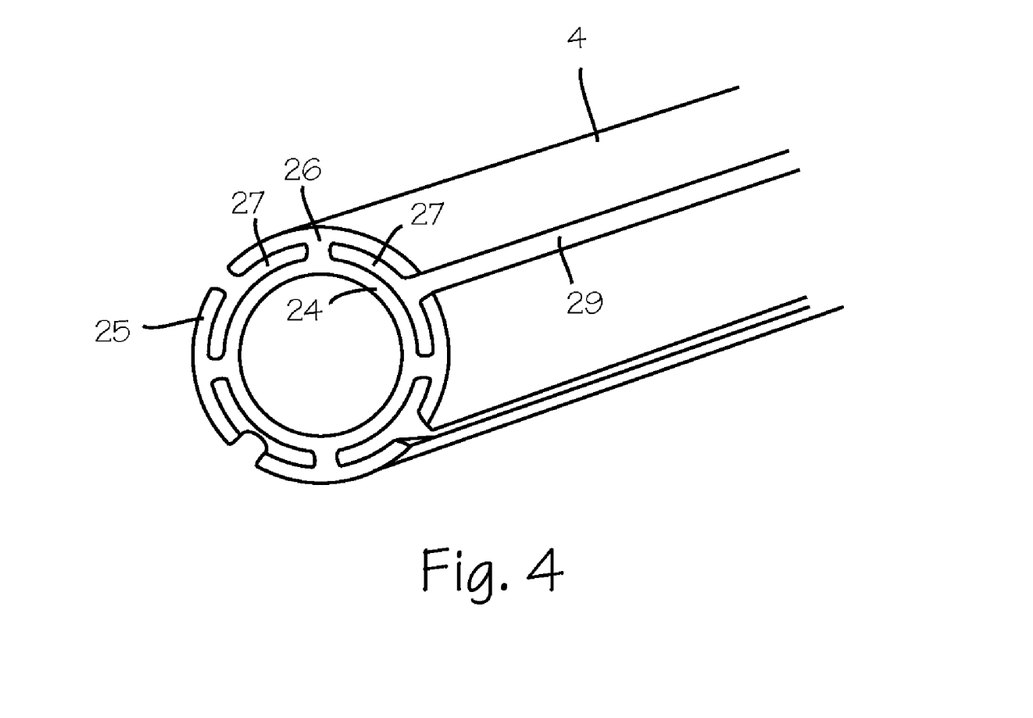
FIG. 4 is a catheter wherein the drainage aperture comprises a longitudinal channel.

FIG. 4 is a sectional view of the proximal portion of the catheter wherein the drainage apertures are comprised of a plurality of longitudinal channels 29. The tube 4 has one or more drainage lumens 27 disposed within the tube and running longitudinally along the catheter tube. A plurality of ribs project from the inner tube 24 to the outer tube 25 forming the plurality of drainage lumens 27. Longitudinal channels are disposed along the proximal portion of the outer tube much like a Blake's drain. Each longitudinal channel communicates with one or more drainage lumens 27 disposed within the tube.

Figure 5:
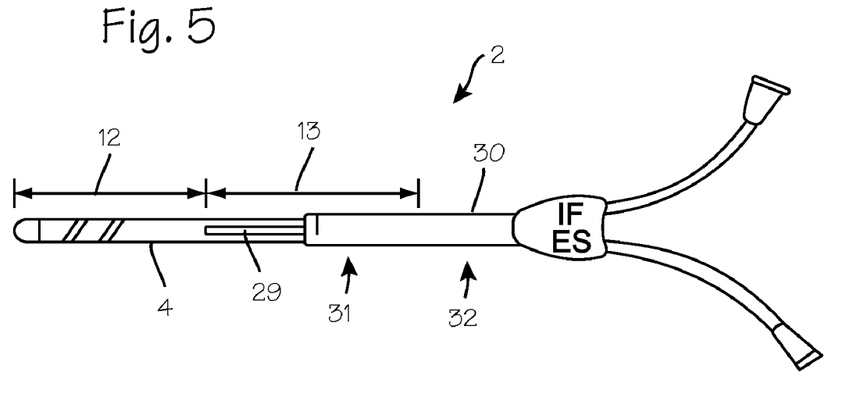
FIG. 5 is an anti-extravasation catheter with an outer sleeve.

FIG. 5 is an anti-extravasation catheter with an outer sleeve. A second tube or outer sleeve 30 is disposed over the outer diameter of the catheter tube to limit exposure of the drainage apertures to the tissue surrounding the insertion point. A first portion 31 of outer sleeve is partially disposed about the proximal section (interstitial portion) of the catheter disposed within the patient. A second portion 32 of the outer sleeve is disposed about that proximal section of the catheter that is not inserted into the patient. Use of one or more outer sleeves 30 limits exposure of the drainage apertures to the tissue surrounding 16 the insertion site. This regulates the amount of fluid that can drain from the tissue.

Figure 6:
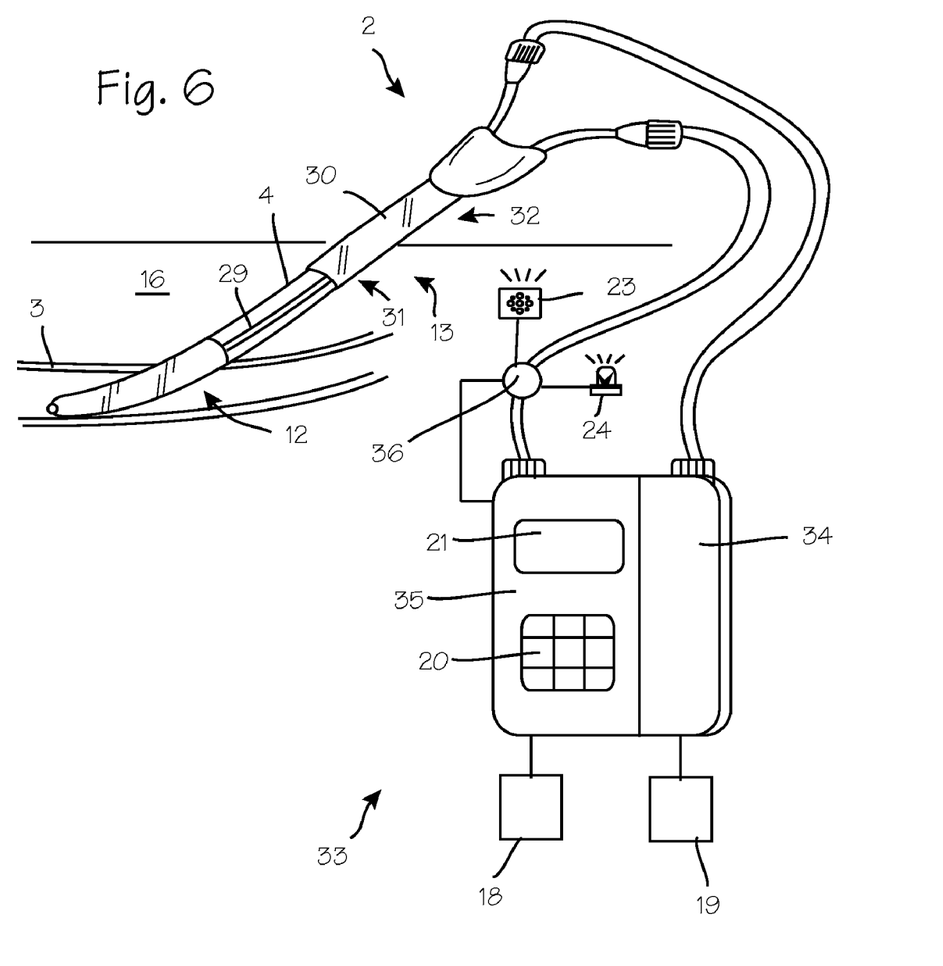
FIG. 6 is a side view of an anti-extravasation catheter with the outer sleeve in use.

FIG. 6 is a side view of the anti-extravasation catheter 2 with the sleeve 30 in use. The catheter is disposed within the peripheral vein of the patient. The outer sleeve 30 is disposed over the outer diameter of the tube 4 to limit exposure of the drainage apertures to the tissue surrounding the insertion site. The first portion 31 of outer sleeve is disposed about that portion of the proximal section of the catheter disposed within the patient. The second portion 32 of the outer sleeve is disposed about the proximal section of the catheter that is not inserted into the patient. The sleeve 30 regulates the exposure of the drainage apertures to the tissue surrounding the insertion point. Tissue 16 surrounding the insertion point and peripheral vein 3 may contain extravasated fluid. The drainage apertures 29 allow this fluid to drain from the tissue and use of the sleeve regulates fluid removal.

The anti-extravasation catheter in FIG. 6 is part of a complete fluid management system 33 comprising infusion pump 34, fluid source 19, vacuum pump 35, vacuum source 18 or sink, and control system 20. The control system may be provided with the display 21, the audio alarm system 22 and/or the visual alarm system 23. The alarm systems are activated when extravasation occurs during the infusion of medicines into the patient 1 The alarm can be triggered by a pressure transducer 36 operably connected to the control system and placed in fluid communication with one or more drainage lumens. Drainage apertures may also be disposed along the substantial length of the tube when the catheter is part of the complete fluid management system or when multiple sleeves are used. When fluid pressure in the drainage lumen exceeds a safe threshold of pressure the control system can activate a vacuum pump located outside and remove fluid from the tissue surround the infusion site.

Figure 7:
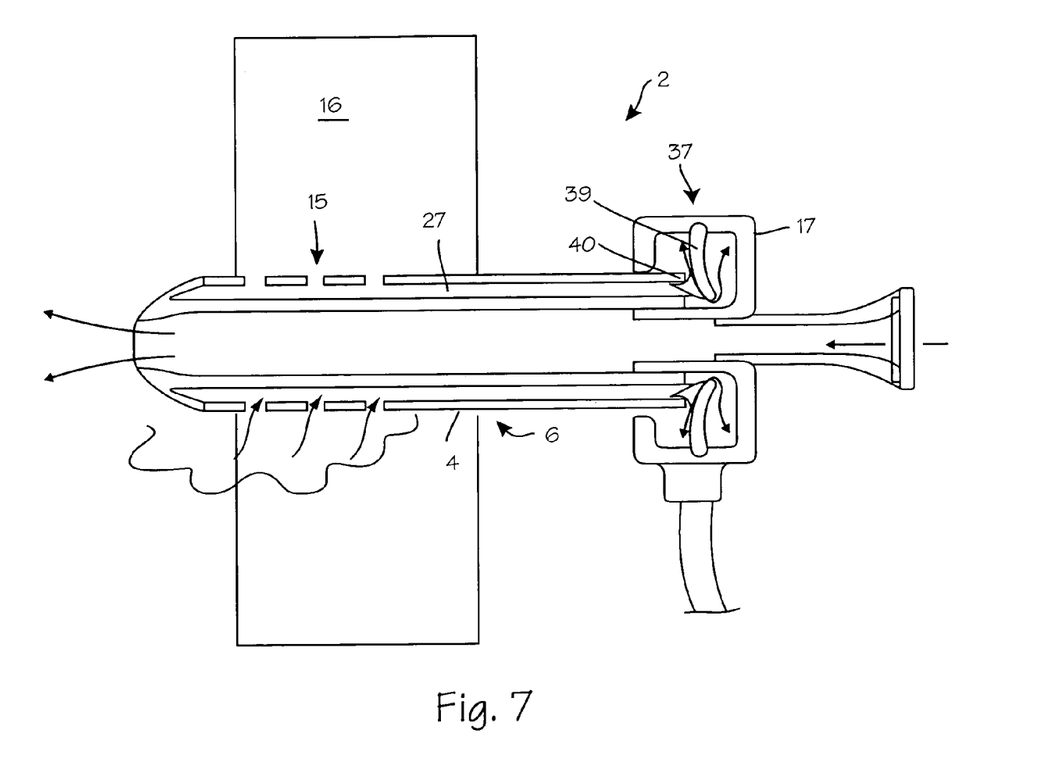
FIG. 7 illustrates an anti-extravasation catheter with an over-pressure valve.

FIG. 7 illustrates the anti-extravasation catheter 2 with an over-pressure valve 37. The valve is operably disposed within the hub 17 and is placed in fluid communication with the drainage apertures 15 through the drainage lumens 27 in the tube 4. The over-pressure valve is a relief valve comprising a flexible closure member 39 having a spring constant sufficient to press the closure member against the valve seat 40 surrounding the drainage lumens 27 until pressure exceeds a predetermined safe threshold. The closure member is an annular membrane and member may be manufactured from a suitable polymer. The proximal section of the closure member 39 is coupled to the hub wall while the distal section presses against the valve seat occluding the drainage lumens 27. The valve allows the drainage lumen 27 in the device to open to the vacuum source and drain extravasated interstitial fluid from tissue 16 when pressure from the fluid exceeds the predetermined pressure threshold. The valve also acts as a barrier to outside contaminants. When fluid pressure in the drainage lumen 27 exceeds a safe threshold, such as a pressure in the range of approximately 1 mm/Hg to about 20 mm/Hg, the valve 37 opens to remove fluid from the tissue surrounding the insertion point 6 and the infusion site.

Figure 8:
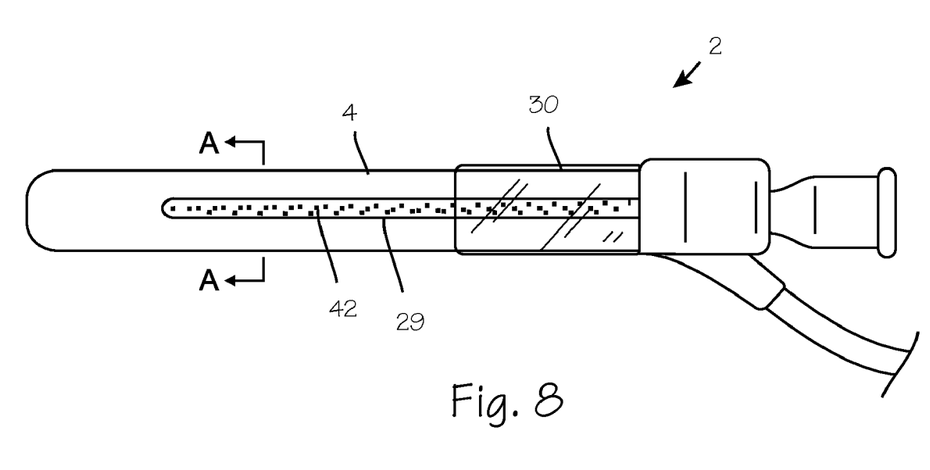
FIG. 8 illustrates the anti-extravasation catheter with the fluid management system comprising a dissolvable plug disposed within the drainage lumen.

FIG. 8 illustrates the anti-extravasation catheter 2 with the fluid management system comprising a dissolvable plug 42 disposed within the drainage lumen. The catheter in FIG. 8 is shown with longitudinal channels 29 and outer sleeve 30. In a fluid management system comprising a dissolvable plug 42, the drainage lumens 27 of the anti-extravasation catheters illustrated in FIGS. 1 through 8 are filed with a dissolvable plug 42 comprising materials that dissolve when the materials come in contact with therapeutic agents being infused into the patent. The dissolvable plug may comprise materials such as starches, gelatins, lactose, sucrose, sugars, or cellulose. The dissolvable plug may be coated with a water-resistant polymer or polysaccharide coating as well. The drainage apertures (longitudinal channel 29) disposed on the tube are placed in fluid communication with tissue surrounding the insertion point when an anti-extravasation catheter is disposed within a patient. Should extravasation of the infused medications occur in the tissue surrounding the insertion point, the infused medications will be placed in contact with the dissolvable plug 42 disposed within the drainage lumens 27. This contact or exposure will cause the dissolvable plug 42 within the drainage lumens to dissolve, opening the drainage lumens and allowing interstitial fluid to drain from the tissue.

Figure 9:
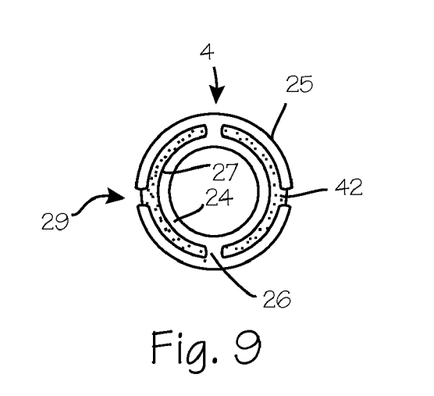
FIG. 9 is a sectional view of the catheter of FIG. 8.

FIG. 9 is a sectional view of the tube 4 with the dissolvable plug. The tube 4 has one or more apertures and one or more drainage lumens 27 disposed within the tube and running longitudinally along the catheter tube. A plurality of ribs 26 project from the inner tube 24 to the outer tube 25 forming the plurality of drainage lumens 27. Longitudinal channels are disposed along the proximal portion of the outer tube much like a Blake's drain. Each longitudinal channel communicates with one or more drainage lumens 27 disposed within the tube.

Figure 10:
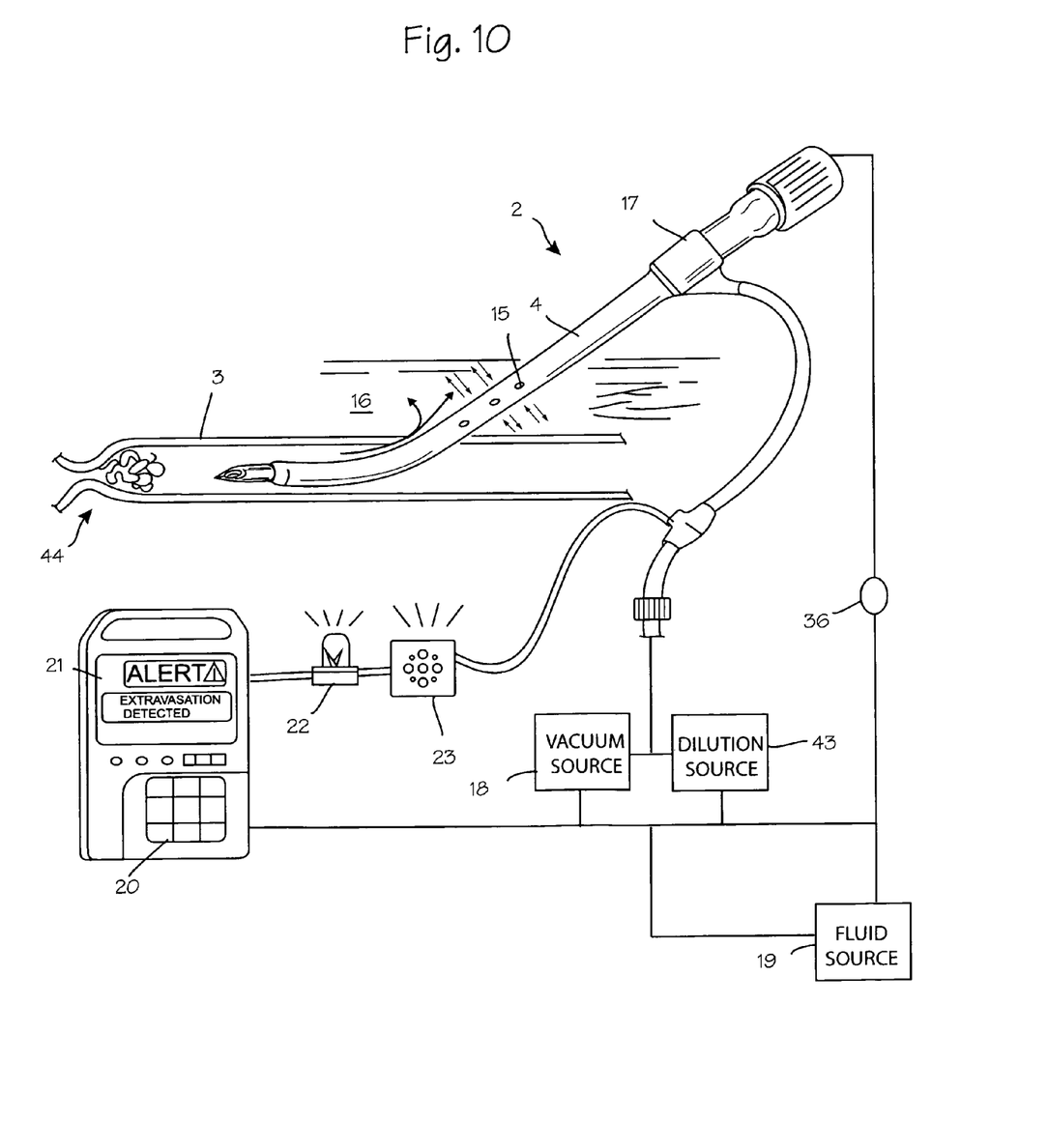
FIG. 10 illustrates the anti-extravasation catheter as part of an irrigation system.

FIG. 10 illustrates the anti-extravasation catheter as part of an irrigation system. Certain therapeutic solutions used in chemotherapy can have detrimental effects on non-cancerous tissue. Flushing and evacuating dangerous infusates may be required should extravasation occur. In an anti-extravasation catheter with an irrigation system, the anti-extravasation catheter of FIGS. 1 through 9 is provided with hub 17 that is suitable for coupling to therapeutic fluid source 19, vacuum source 18 and an antidote or dilution source 43. An antidote is a compound that blocks or attenuates the local tissue toxicity caused by a therapeutic fluid or agent. The vacuum source and dilution source are placed in fluid communication with one or more drainage lumens through the hub 17. Thus, the drainage lumens can function as inflow and/or outflow lumens. Pressure transducer 36 is operably connected to control system 20 and the central lumen of the tube 4. The transducer 36 is able to measure pressure in the vein of the patient. Other sensors that may detect extravasation may be provided with the anti-extravasation catheter and operably coupled to the catheter including electrical impedance sensors, Ph sensors, optical sensors or tissue temperature sensors. (The infiltration of an infusate into interstitial tissue may result in one or more changes in impedance, Ph or temperature.)

Extravasation can result from a thrombosed or collapsed vein 44. A collapsed vein will cause a pressure increase within the vein of the patient due to the backflow of an infusate. When a pressure increase exceeding an acceptable threshold is detected by pressure transducer 36, the control system 20 may operate a pump operably coupled to the dilution source to flush the surrounding tissue. Tissue 16 is flushed using the fluid from the dilution source that is placed in fluid communication with the tissue through one or more drainage lumens and one or more drainage apertures. The control system can also operate the vacuum source to aspirate the interstitial fluid from the tissue. Interstitial fluid is removed through one or more drainage apertures in fluid communication with the drainage lumens and the vacuum source. The control system can be programmed to perform cycles of infusion and aspiration to more completely dilute and remove harmful agents from the soft tissue surround the insertion point of the catheter. A display 21 as well as an audio 22 and/or visual 23 warning system that indicates when extravasation is occurring may also be provided with the control system.

Current prior art catheters used in chemotherapeutic sessions do not provide for the removal of interstitial fluid while simultaneously infusing therapeutic agents into a patient. The anti-extravasation catheter 2 is especially suitable for the infusion of therapeutic agents used in chemotherapy. When the catheter is in use, the physician provides the anti-extravasation catheter 2 with at least one drainage aperture 15 disposed on the proximal portion of the catheter. The catheter is inserted into the vein of a patient at the insertion point 6. The catheter 2 extends from the insertion point to the infusion site 7 when functionally disposed with the patient 1. The catheter 2 is disposed inside the patient 1 in such a way that the drainage aperture 15 is placed in fluid communication with tissue 16 surrounding the vein 3 and the insertion point 6.

The catheter 2 is operably connected to a therapeutic solution/fluid source 19 and a vacuum source 19 through the hub 17. During chemotherapy, the therapeutic solution is infused into the patient through the catheter. During the infusion, extravasation may occur by fluid leaking from the infusion site into tissue surrounding the vein and the insertion point. This extravasated fluid is drained from tissue surrounding the catheter insertion point and the vein 3 during a chemotherapeutic session through the drainage aperture. The tissue 16 may also be treated by an antidote that is provided through the aperture if necessary.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. An anti-extravasation system comprising:
a catheter having a length and an outer diameter suitable for extending from a peripheral vein insertion point on a patient to a treatment site, said catheter characterized by an elongated venous section located distal to an interstitial section and comprising:
an inner tube characterized by central lumen;
an outer tube disposed about the inner tube;
a plurality of ribs extending between the inner and outer tubes and running along the length of the catheter;
wherein the inner tube, the outer tube and the plurality of ribs bound a plurality of drainage lumens that extend between the inner and outer tubes and that run along the length of the catheter; and a plurality of apertures disposed in the interstitial section of the outer tube, said apertures in fluid communication with the drainage lumens and adapted to drain fluid from tissue surrounding the insertion point when the catheter is operably disposed within the patient;

wherein the venous section of the outer tube comprises an outer surface and is structured to prevent fluid communication between the outer surface of the venous section and the drainage lumens; and a hub proximal to the interstitial section and placed in fluid communication with the central lumen and the plurality of drainage lumens.

2. The system of claim 1 wherein the catheter is sized and dimensioned such that the interstitial section resides in body tissue overlying the insertion point in a peripheral vein and the venous section of the catheter resides in the central venous system of the patient when disposed within the patient.

3. The system of claim 1 wherein the catheter is sized and dimensioned such that the interstitial section resides in body tissue overlying the insertion point in a peripheral vein and the venous section of the catheter resides in the peripheral vein.

4. The system of claim 1 wherein the apertures comprise longitudinal channels.

5. The system of claim 1 wherein the apertures comprise fenestrations.

6. The system of claim 1 further comprising an extravasation sensor operably coupled to the catheter, said sensor selected from the group consisting of a temperature sensor, a pressure sensor, a conductivity sensor, an optical sensor and a Ph sensor.

7. The system of claim 6 further comprising a control system operably coupled to the catheter, said control system adapted to detect the occurrence of extravasation and alert a user when extravasation occurs.

8. The system of claim 1 further comprising a dissolvable plug disposed within one or more drainage lumens.

9. The system of claim 8 wherein the dissolvable plug comprises a material selected from the group consisting of starches, gelatins, lactose, sucrose, sugars and cellulose.

10. The system of claim 1 further comprising an overpressure valve in fluid communication with one or more drainage lumens.

11. The system of claim 1 further comprising an outer sleeve disposed over an outer diameter of the outer tube.

12. The system of claim 1 further comprising an anti-extravasation agent source placed in fluid communication with one or more outer lumens.

* * * * *